United States Patent [19]
Bittner et al.

[11] Patent Number: 6,024,768
[45] Date of Patent: Feb. 15, 2000

[54] DIAMINOALKANE AND OXIDATION COLORANTS

[75] Inventors: Andreas Joachim Bittner, Offenbach; Astrid Kleen, Erkrath, both of Germany

[73] Assignee: Hans Schwarzkopf GmbH & Co. KG, Hamburg, Germany

[21] Appl. No.: 09/214,218

[22] PCT Filed: Jul. 2, 1997

[86] PCT No.: PCT/EP97/03466

§ 371 Date: Apr. 6, 1999

§ 102(e) Date: Apr. 6, 1999

[87] PCT Pub. No.: WO98/01418

PCT Pub. Date: Jan. 15, 1998

[30] Foreign Application Priority Data

Jul. 3, 1996 [DE] Germany ............ 196 26 740
Jul. 3, 1996 [DE] Germany ............ 196 26 743

[51] Int. Cl.⁷ ............ A61K 7/13; C07C 211/54
[52] U.S. Cl. ............ 8/410; 8/407; 8/408; 8/416; 8/649; 564/367; 564/428
[58] Field of Search .............. 564/428, 367; 8/407, 408, 410, 416, 649

[56] References Cited

U.S. PATENT DOCUMENTS

| | | | |
|---|---|---|---|
| 3,694,138 | 9/1972 | Kalopissis et al. | 8/408 |
| 3,817,698 | 6/1974 | Kalopissis et al. | 8/405 |
| 4,010,200 | 3/1977 | Kalopissis et al. | 564/367 |
| 4,842,612 | 6/1989 | Rose et al. | 8/411 |
| 4,865,774 | 9/1989 | Fabry et al. | 510/428 |
| 4,931,218 | 6/1990 | Schenker et al. | 510/498 |
| 5,114,429 | 5/1992 | Junino et al. | 8/410 |
| 5,294,726 | 3/1994 | Behler et al. | 554/98 |
| 5,676,706 | 10/1997 | Akram et al. | 8/416 |

FOREIGN PATENT DOCUMENTS

| | | |
|---|---|---|
| 0 286 896 | 10/1988 | European Pat. Off. |
| 0 358 550 | 3/1990 | European Pat. Off. |
| 0 709 365 | 5/1996 | European Pat. Off. |
| 19 39 062 | 4/1970 | Germany. |
| 37 23 354 | 1/1989 | Germany. |
| 37 25 030 | 2/1989 | Germany. |
| 39 26 344 | 2/1991 | Germany. |

*Primary Examiner*—Caroline D. Liott
*Attorney, Agent, or Firm*—Ernest Szoke; Wayne C. Jaeschke; Glenn E.J. Murphy

[57] ABSTRACT

A diaminoalkane of general formula (I) in which $R_1$ to $R_{10}$ stand independently of each other for hydrogen, a $(C_1–C_4)$-alkyl group, a hydroxy-$(C_2–C_3)$-alkyl group, a $(C_1–C_4)$-alkoxy-$(C_2–C_3)$ alkyl group, an amino-$(C_2–C_3)$ alkyl group or a 2,3-dihydroxypropyl group and n is a number from 1 to 6 with the proviso that the $—NR_1R_2$ and $—NR_7R_8$ groups are either in positions 4 and 4' or in positions 5 and 5'. Salts of the diaminoalkane which are physiologically compatible with inorganic and organic acids. Method of coloring keratin fiber.

21 Claims, No Drawings

DIAMINOALKANE AND OXIDATION COLORANTS

BACKGROUND OF THE INVENTION

This invention relates to new diaminoalkanes and to oxidation colorants containing these compounds.

By virtue of their intensive colors and good fastness properties, so-called oxidation colorants play a prominent role in the coloring of keratin fibers, particularly human hair. Oxidation colorants normally contain oxidation dye precursors, so-called primary intermediates and secondary intermediates. The primary intermediates form the actual dyes with one another or by coupling with one or more secondary intermediates in the presence of oxidizing agents or atmospheric oxygen.

Good oxidation dyes (precursors) are expected to satisfy above all the following requirements: they must form the required color tones with sufficient intensity and fastness during the oxidative coupling reaction. In addition, they must be readily absorbed onto the fibers with no significant differences—particularly in the case of human hair—between damaged and freshly regrown hair (levelling behavior). They must be resistant to light, heat and the effect of chemical reducing agents, for example permanent wave lotions. Finally, if they are used to color hair, they should not overly stain the scalp and, above all, should be toxicologically and dermatologically safe.

The primary intermediates used are, for example, primary aromatic amines containing another free or substituted hydroxy or amino group in the para position or the ortho position, diaminopyridine derivatives, heterocyclic hydrazones, 4-aminopyrazolone derivatives and 2,4,5,6-tetraaminopyrimidine and derivatives thereof.

The secondary intermediates are generally m-phenylenediamine derivatives, naphthols, resorcinol and resorcinol derivatives, pyrazolones, m-aminophenols and pyridine derivatives. With regard to the individual dye components suitable for use in accordance with the invention, reference is specifically made to the Colipa List published by the Industrieverband Körperpflege und Waschmittel, Frankfurt.

In general, natural color tones cannot be obtained with a single secondary intermediate/primary intermediate combination. In practice, therefore, a combination of various primary intermediates and secondary intermediates has to be used to obtain a natural-looking color.

Thus, many intensive blue color tones obtainable with the known primary intermediate/secondary intermediate combinations contain a distinct red component. This red component is a disadvantage, particularly in the case of lighter shades, but also for obtaining natural shades which are intended to have an adequate depth of color and an adequate grey-covering effect.

Accordingly, there is still a need for primary intermediate/secondary intermediate combinations which produce an intensive color in the clear blue range and, more particularly, a pure black tone with no tinges of blue or red.

In addition, the risk of an uneven coloring result, poorer levelling behavior and less favorable fastness properties also increases with increasing number of the oxidation dye precursors used.

Accordingly, there is still a need for new oxidation dye precursors which, in particular, even enable natural colors to be obtained using a smaller number of dye precursors.

Accordingly, the problem addressed by the present invention was to provide new compounds which would satisfy the requirements oxidation dye precursors are expected to meet to a particular degree.

DESCRIPTION OF THE INVENTION

It has now surprisingly been found that, by virtue of their particular electronic structure, the compounds of general formula (I) described in the present invention satisfy these requirements particularly well. In particular, "pure black" colors can be obtained with them. In addition, these compounds surprisingly show both pronounced secondary intermediate properties and pronounced primary intermediate properties. As a result, a large number of color tones can be obtained with a small number of other oxidation dye precursors of the secondary intermediate and/or primary intermediate type without the levelling and fastness problems often observed where relatively large numbers of oxidation dye precursors are used occurring.

In a first embodiment, therefore, the present invention relates to diaminoalkanes corresponding to general formula (I):

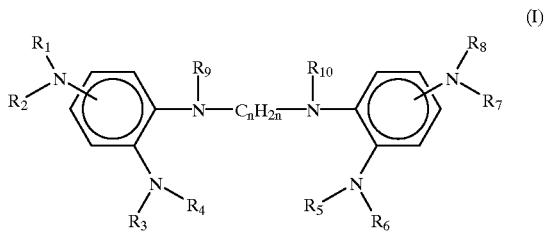

in which $R_1$ to $R_{10}$ independently of one another represent hydrogen,
a $(C_{1-4})$-alkyl group,
a hydroxy-$(C_{2-3})$-alkyl group,
a $(C_{1-4})$-alkoxy-$(C_{2-3})$-alkyl group,
an amino-$(C_{2-3})$-alkyl group or
a 2,3-dihydroxypropyl group and
n is an integer of 1 to 6,
with the proviso that the groups —$NR_1R_2$ and —$NR_7R_8$ are either in positions 4 and 4' or in positions 5 and 5', and physiologically compatible salts thereof with inorganic and organic acids.

Similar compounds and their use in oxidation colorants are known from EP-A2-0 286 896. However, the compounds which have now been found are distinctly superior in their coloring properties to those compounds. One reason for this could be the symmetrical substitution pattern, particularly if the substituents at the two phenyl rings are also identical, at least in pairs. At all events, the cited document does not provide any indication of the excellent coloring properties of the compounds which have now been found.

Compounds in which on the one hand the groups —$NR_1R_2$ and —$NR_7R_8$ and on the other hand the groups —$NR_3R_4$ and —$NR_5R_6$ are identical show particularly outstanding properties.

Preferred substituents $R_1$ to $R_8$ are hydrogen, methyl, ethyl, 2-hydroxyethyl, 2-aminoethyl and 2,3-dihydroxypropyl groups.

Preferred substituents $R_9$ and $R_{10}$ are hydrogen.

Preferred —$C_nH_{2n}$— groups are linear 1,n-alkylene groups, more particularly with n=2 and 3. According to the invention, therefore, preferred compounds are derivatives of 1,2-diaminoethane or 1,3-diaminopropane.

The compounds corresponding to formula (I) may be present both as free bases and in the form of their physiologically compatible salts with inorganic or organic acids, for example hydrochlorides, sulfates and hydrobromides. Other acids suitable for salt formation are phosphoric acid and also acetic acid, propionic acid, lactic acid and citric acid. Accordingly, the following observations on the compounds corresponding to formula (I) always apply to these salts also.

The compounds (I) may be prepared by known methods. Specific reference is made in this regard to the Examples of the present specification.

The compounds corresponding to formula (I) are eminently suitable as oxidation dye precursors.

Accordingly, the present invention relates to oxidation colorants for coloring keratin fibers which contain compounds corresponding to formula (I) as oxidation dye precursors.

Keratin fibers in the context of the invention are pelts, wool, feathers and, in particular, human hair. Although the oxidation colorants according to the invention are primarily suitable for coloring kerating fibers, there is nothing in principle to stop them being used in other fields, particularly in color photography.

The colorants according to the invention contain a compound corresponding to formula (I) in claim 1 as oxidation dye precursor as a compulsory component. Particularly outstanding coloring results have been obtained with compounds of formula (I) which are symmetrical in structure, i.e. in which on the one hand the groups —$NR_1R_2$ and —$NR_7R_8$ and on the other hand the groups —$NR_3R_4$ and —$NR_5R_6$ are identical. So far as the preferred substituents are concerned, reference is made to the foregoing observations.

The hair colorants according to the invention contain the compounds corresponding to formula (I) in a quantity of preferably 0.001 to 10% by weight and, more preferably, 0.1 to 5% by weight, based on the oxidation colorant as a whole. Both here and in the following, the expressions "oxidation colorant as a whole" or "colorant as a whole" refer to the product which is presented to the user. Depending upon the particular formulation, this product may be applied to the hair either directly or after mixing with water or, for example, an aqueous solution of an oxidizing agent.

The compounds corresponding to formula (I) may act both as primary intermediates and as secondary intermediates in the oxidation colorants according to the invention.

In a first embodiment, the colorants according to the invention only contain the compounds of formula (I) as oxidation dye precursors.

However, the number of shades obtainable is distinctly increased if, in addition to the compounds of formula (I), the colorant also contains at least one other oxidation dye precursor.

In a second preferred embodiment, therefore, the colorants according to the invention additionally contain at least one other oxidation dye precursor of the secondary intermediate type.

According to the invention, preferred secondary intermediates are 1-naphthol, pyrogallol, 1,5-, 2,7- and 1,7-dihydroxynaphthalene, o-amino-phenol, 5-amino-2-methylphenol, m-aminophenol, resorcinol, resorcinol monomethyl ether, m-phenylene diamine, 1-phenyl-3-methyl-5-pyrazolone, 2,4-dichloro-3-aminophenol, 1,3-bis-(2,4-diaminophenoxy)-propane, 4-chlororesorcinol, 2-chloro-6-methyl-3-aminophenol, 2-methyl resorcinol, 5-methyl resorcinol, 2,5-dimethyl resorcinol, 2,6-dihydroxypyridine, 2,6-diaminopyridine, 2-amino-3-hydroxypyridine, 2,6-dihydroxy-3,4-diaminopyridine, 3-amino-2-methylamino6-methoxypyridine, 4-amino-2-hydroxytoluene, 2,6-bis-(2-hydroxyethylamino)-toluene, 2,4-diaminophenoxyethanol, 2-amino-4-hydroxyethylaminoanisole.

According to the invention, 1,7-dihydroxynaphthalene, m-aminophenol, 2-methyl resorcinol, 4-amino-2-hydroxytoluene, 2-amino-4-hydroxyethylaminoanisole and 2,4-diaminophenoxyethanol are particularly preferred.

This embodiment does of course also encompass the use of several additional secondary intermediates. According to the invention, preferred secondary intermediate combinations are resorcinol, m-phenylene diamine, 4-chlororesorcinol, 2-amino-4-hydroxyethylaminoanisole, 2-methyl resorcinol, 4-chlororesorcinol, 2-amino-3-hydroxypyridine, resorcinol, m-aminoaniline, 2-hydroxy-4-aminotoluene, 3-methyl-4-aminoaniline, m-aminoaniline, 2-hydroxy-4-aminotoluene, 2-amino-3-hydroxypyridine, 2-methyl resorcinol, m-aminoaniline, 2-hydroxy-4-aminotoluene, 2-amino-3-hydroxypyridine.

In a second preferred embodiment, therefore, the colorants according to the invention optionally contain at least one other oxidation dye precursor of the primary intermediate type in addition one other oxidation dye precursor of the secondary intermediate type.

According to the invention, preferred primary intermediates are p-phenylene diamine, p-toluylene diamine, p-aminophenol, 3-methyl-1,4-diaminobenzene, 1-(2'-hydroxyethyl)-2,5-diaminobenzene, N,N-bis-(2-hydroxyethyl)-p-phenylene diamine, 2-(2,5-diaminophenoxy)-ethanol, 1-phenyl-3-carboxyamido-4-amino-5-pyrazolone, 4-amino-3-methyl phenol, 2-methylamino4-aminophenol, 2,4,5,6-tetraaminopyrimidine, 2-hydroxy-4,5,6-triaminopyrimidine, 4-hydroxy-2,5,6-triaminopyrimidine, 2,4-dihydroxy-5,6-diaminopyrimidine, 2-dimethylamino-4,5,6-triaminopyrimidine and 2-hydroxyethylaminomethyl-4-aminophenol.

According to the invention, p-toluylene diamine, p-aminophenol, 1-(2'-hydroxyethyl)-2,5-diaminobenzene, 4-amino-3-methylphenol, 2-methylamino-4-aminophenol and 2,4,5,6-tetraaminopyrimidine are most particularly preferred.

This embodiment does of course also encompass the use of several additional primary intermediates. According to the invention, preferred primary intermediate combinations are p-toluylene diamine, p-phenylene diamine, 3-methyl4-aminoaniline, p-toluylene diamine, p-toluylene diamine, 4-amino-3-methylphenol, p-toluylene diamine, 2-methylamino-4-aminophenol, 2,4,5,6-tetraaminopyrimidine, 1-(2'-hydroxyethyl)-2,5-diaminobenzene, 2,4,5,6-tetraaminopyrimidine, p-toluylene diamine.

The primary and secondary intermediates are normally used in a substantially equimolar ratio to one another. Although it has proved to be useful to employ the primary and secondary intermediates in an equimolar ratio, a certain excess of individual oxidation dye precursors is by no means a disadvantage, so that the primary and secondary intermediates may advantageously be present in the colorant in a molar ratio of 1:0.5 to 1:2. The total quantity of oxidation dye precursors is generally at most 20% by weight, based on the colorant as a whole.

In a fourth, likewise preferred embodiment, the colorants according to the invention optionally contain substantive dyes in addition to other oxidation dye precursors for further modifying the color tones. The substantive dyes in question belong, for example, to the group consisting of nitrophenylenediamines, nitroaminophenols, anthraquinones or indophenols. Preferred substantive dyes are the compounds known under the International names or commercial names of HC Yellow 2, HC Yellow 4, Basic Yellow 57, Disperse Orange 3, HC Red 3, HC Red BN, Basic Red 76, HC Blue 2, Disperse Blue 3, Basic Blue 99, HC Violet 1, Disperse Violet 1, Disperse Violet 4, Disperse Black 9, Basic Brown 16, Basic Brown 17, picramic acid and Rodol R and also 4-amino-2-nitrodiphenylamine-2'-carboxylic acid, 6-nitro-1,2,3,4-tetrahydroquinoxaline, (N-2,3-dihydroxypropyl-2-nitro-4-trifluoromethyl)-aminobenzene and 4-N-ethyl-1,4-bis-(2'-hydroxyethylamino)-2-nitrobenzene hydrochloride. The colorants according to this embodiment of the invention contain the substantive dye in a quantity of preferably 0.01 to 20% by weight, based on the colorant as a whole.

In addition, the colorants according to the invention may also contain naturally occurring dyes such as, for example, henna red, henna neutral, henna black, camomile blossom, sandalwood, black tea, black alder bark, sage, logwood, madder root, catechu, sedre and alkanet.

The oxidation dye precursors compulsorily or optionally present do not have to be single compounds. Instead, the hair colorants according to the invention—due to the processes used for producing the individual dyes—may contain small quantities of other components providing they do not adversely affect the coloring result or have to be ruled out for other reasons, for example toxicological reasons.

Typical formulations for the oxidation colorants according to the invention are preparations based on water or non-aqueous solvents and powders.

In one preferred embodiment for the production of the colorants according to the invention, the oxidation dye precursors are incorporated in a suitable water-containing carrier. For coloring hair, such carriers are, for example, cremes, emulsions, gels or even surfactant-containing foaming solutions, for example shampoos, foam aerosols or other formulations suitable for application to the hair. The hair colorants according to the invention are adjusted to a pH value of preferably 6.5 to 11.5 and, more preferably, 9 to 10.

The colorants according to the invention may also contain any of the known active substances, additives and auxiliaries typical of such formulations. In many cases, the colorants contain at least one surfactant, both anionic and zwitterionic, ampholytic, nonionic and cationic surfactants being suitable in principle. In many cases, however, it has been found to be of advantage to select the surfactants from anionic, zwitterionic or nonionic surfactants. Anionic surfactants can be particularly useful.

Suitable anionic surfactants for the preparations according to the invention are any anionic surface-active substances suitable for use on the human body. Such substances are characterized by a water-solubilizing anionic group such as, for example, a carboxylate, sulfate, sulfonate or phosphate group and a lipophilic alkyl group containing around 10 to 22 carbon atoms. In addition, glycol or polyglycol ether groups, ether, amide and hydroxyl groups and—generally—ester groups may also be present in the molecule. The following are examples of suitable anionic surfactants—in the form of the sodium, potassium and ammonium salts and the mono-, di- and trialkanolammonium salts containing 2 or 3 carbon atoms in the alkanol group:

linear and branched fatty acids containing 8 to 22 carbon atoms (soaps), ether carboxylic acids corresponding to the formula R—O—(CH$_2$—CH$_2$O)$_x$—CH$_2$—COOH, in which R is a linear alkyl group containing 10 to 22 carbon atoms and x=0 or 1 to 16, acyl sarcosides containing 10 to 18 carbon atoms in the acyl group, acyl taurides containing 10 to 18 carbon atoms in the acyl group, acyl isethionates containing 10 to 18 carbon atoms in the acyl group, sulfosuccinic acid mono- and dialkyl esters containing 8 to 18 carbon atoms in the alkyl group and sulfosuccinic acid monoalkyl polyoxyethyl esters containing 8 to 18 carbon atoms in the alkyl group and 1 to 6 oxyethyl groups, linear alkane sulfonates containing 12 to 18 carbon atoms, linear α-olefin sulfonates containing 12 to 18 carbon atoms, α-sulfofatty acid methyl esters of fatty acids containing 12 to 18 carbon atoms, alkyl sulfates and alkyl polyglycol ether sulfates corresponding to the formula R—O(CH$_2$—CH$_2$O)$_x$—SO$_3$H, in which R is a preferably linear alkyl group containing 10 to 18 carbon atoms and x=0 or 1 to 12, mixtures of surface-active hydroxysulfonates according to DE-A-37 25 030, sulfated hydroxyalkyl polyethylene and/or hydroxyalkylene propylene glycol ethers according to DE-A-37 23 354, sulfonates of unsaturated fatty acids containing 12 to 24 carbon atoms and 1 to 6 double bonds according to DE-A-39 26 344, esters of tartaric acid and citric acid with alcohols in the form of addition products of around 2 to 15 molecules of ethylene oxide and/or propylene oxide with fatty alcohols containing 8 to 22 carbon atoms.

Preferred anionic surfactants are alkyl sulfates, alkyl polyglycol ether sulfates and ether carboxylic acids containing 10 to 18 carbon atoms in the alkyl group and up to 12 glycol ether groups in the molecule and, in particular, salts of saturated and, more particularly, unsaturated C$_{8-22}$ carboxylic acids, such as oleic acid, stearic acid, isostearic acid and palmitic acid.

In the context of the invention, zwitterionic surfactants are surface-active compounds which contain at least one quaternary ammonium group and at least one —COO$^{(-)}$ or —SO$_3^{(-)}$ group in the molecule. Particularly suitable zwitterionic surfactants are the so-called betaines, such as N-alkyl-N,N-dimethyl ammonium glycinates, for example cocoalkyl dimethyl ammonium glycinate, N-acylaminopropyl-N, N-dimethyl ammonium glycinates, for example cocoacylaminopropyl dimethyl ammonium glycinate, and 2-alkyl-3-carboxymethyl-3-hydroxyethyl imidazolines containing 8 to 18 carbon atoms in the alkyl or acyl group and cocoacylaminoethyl hydroxyethyl carboxymethyl glycinate. A preferred zwitterionic surfactant is the fatty acid amide derivative known by the CTFA name of Cocamidopropyl Betaine.

Ampholytic surfactants are surface-active compounds which, in addition to a C$_{8-18}$ alkyl or acyl group, contain at least one free amino group and at least one —COOH or —SO$_3$H group in the molecule and which are capable of forming inner salts. Examples of suitable ampholytic surfactants are N-alkyl glycines, N-alkyl propionic acids, N-alkyl aminobutyric acids, N-alkyl iminodipropionic acids, N-hydroxyethyl-N-alkyl amidopropyl glycines, N-alkyl taurines, N-alkyl sarcosines, 2-alkyl aminopropionic acids and alkyl aminoacetic acids containing around 8 to 18 carbon atoms in the alkyl group. Particularly preferred ampholytic surfactants are N-cocoalkyl aminopropionate, cocoacyl aminoethyl aminopropionate and $C_{12-18}$ acyl sarcosine.

Nonionic surfactants contain, for example, a polyol group, a polyalkylene glycol ether group or a combination of polyol and polyglycol ether groups as the hydrophilic group. Examples of such compounds are

- products of the addition of 2 to 30 moles of ethylene oxide and/or 0 to 5 moles of propylene oxide to linear fatty alcohols containing 8 to 22 carbon atoms, to fatty acids containing 12 to 22 carbon atoms and to alkylphenols containing 8 to 15 carbon atoms in the alkyl group,
- $C_{12-22}$ fatty acid monoesters and diesters of products of the addition of 1 to 30 moles of ethylene oxide to glycerol,
- $C_{8-22}$ alkyl mono- and oligoglycosides and ethoxylated analogs thereof,
- products of the addition of 5 to 60 moles of ethylene oxide to castor oil and hydrogenated castor oil,
- products of the addition of ethylene oxide to sorbitan fatty acid esters,
- products of the addition of ethylene oxide to fatty acid alkanolamides.

Examples of cationic surfactants suitable for use in the hair treatment formulations according to the invention are, in particular, quaternary ammonium compounds. Preferred quaternary ammonium compounds are ammonium halides, such as alkyl trimethyl ammonium chlorides, dialkyl dimethyl ammonium chlorides and trialkyl methyl ammonium chlorides, for example cetyl trimethyl ammonium chloride, stearyl trimethyl ammonium chloride, distearyl dimethyl ammonium chloride, lauryl dimethyl ammonium chloride, lauryl dimethyl benzyl ammonium chloride and tricetyl methyl ammonium chloride. Other cationic surfactants suitable for use in accordance with the invention are the quaternized protein hydrolyzates.

Also suitable for use in accordance with the invention are cationic silicone oils such as, for example, the commercially available products Q2-7224 (manufacturer: Dow Corning; a stabilized trimethyl silyl amodimethicone), Dow Corning® 929 Emulsion (containing a hydroxylamino-modified silicone which is also known as Amodimethicone), SM-2059 (manufacturer: General Electric), SLM-55067 (manufacturer: Wacker) and Abil®-Quat 3270 and 3272 (manufacturer: Th. Goldschmidt; diquaternary polydimethyl siloxanes, Quaternium-80).

Alkyl amidoamines, particularly fatty acid amidoamines, such as the stearyl amidopropyl dimethyl amine obtainable as Tego Amid®S 18, are distinguished not only by their favorable conditioning effect, but also and in particular by their ready biodegradability.

Quaternary ester compounds, so-called "esterquats", such as the dialkyl ammonium methosulfates and methyl hydroxyalkyl dialkoyloxyalkyl ammonium methosulfates marketed under the trade name of Stepantex®, are also readily biodegradable.

One example of a quaternary sugar derivative suitable for use as a cationic surfactant is the commercially available product Glucquat®100 (CTFA name: Lauryl Methyl Gluceth-10 Hydroxypropyl Dimonium Chloride).

The compounds containing alkyl groups used as surfactants may be single compounds. In general, however, these compounds are produced from native vegetable or animal raw materials so that mixtures with different alkyl chain lengths dependent upon the particular raw material are obtained.

The surfactants representing addition products of ethylene and/or propylene oxide with fatty alcohols or derivatives of these addition products may be both products with a "normal" homolog distribution and products with a narrow homolog distribution. Products with a "normal" homolog distribution are mixtures of homologs which are obtained in the reaction of fatty alcohol and alkylene oxide using alkali metals, alkali metal hydroxides or alkali metal alcoholates as catalysts. By contrast, narrow homolog distributions are obtained when, for example, hydrotalcites, alkaline earth metal salts of ether carboxylic acids, alkaline earth metal oxides, hydroxides or alcoholates are used as catalysts. The use of products with a narrow homolog distribution can be of advantage.

Other active substances, auxiliaries and additives are, for example,

- nonionic polymers such as, for example, vinyl pyrrolidone/vinyl acrylate copolymers, polyvinyl pyrrolidone and vinyl pyrrolidone/vinyl acetate copolymers and polysiloxanes,
- cationic polymers, such as quaternized cellulose ethers, polysiloxanes containing quaternary groups, dimethyl diallyl ammonium chloride polymers, acrylamide/dimethyl diallyl ammonium chloride copolymers, dimethyl aminoethyl methacrylate/vinyl pyrrolidone copolymers quaternized with diethyl sulfate, vinyl pyrrolidone/imidazolinium methochloride copolymers and quaternized polyvinyl alcohol,
- zwitterionic and amphoteric polymers such as, for example, acrylamidopropyl/trimethyl ammonium chloride/acrylate copolymers and octyl acrylamide/methyl methacrylate/tert.butyl aminoethyl methacrylate/2-hydroxypropyl methacrylate copolymers,
- anionic polymers such as, for example, polyacrylic acids, crosslinked polyacrylic acids, vinyl acetate/crotonic acid copolymers, vinyl pyrrolidone/vinyl acrylate copolymers, vinyl acetate/butyl maleate/isobornyl acrylate copolymers, methyl vinyl ether/maleic anhydride copolymers and acrylic acid/ethyl acrylate/N-tert.butyl acrylamide terpolymers,
- thickeners, such as agar agar, guar gum, alginates, xanthan gum, gum arabic, karaya gum, carob bean flour, linseed gums, dextrans, cellulose derivatives, for example methyl cellulose, hydroxyalkyl cellulose and carboxymethyl cellulose, starch fractions and derivatives, such as amylose, amylopectin and dextrins, clays such as, for example, bentonite or fully synthetic hydrocolloids such as, for example, polyvinyl alcohol,
- structurants, such as glucose, maleic acid and lactic acid,
- hair-conditioning compounds, such as phospholipids, for example soya lecithin, egg lecithin and kephalins, and also silicone oils,
- protein hydrolyzates, more particularly elastin, collagen, keratin, milk protein, soya protein and wheat protein hydrolyzates, condensation products thereof with fatty acids and quaternized protein hydrolyzates,
- perfume oils, dimethyl isosorbide and cyclodextrins,
- solubilizers, such as ethanol, isopropanol, ethylene glycol, propylene glycol, glycerol and diethylene glycol, antidandruff agents, such as Piroctone Olamine and Zinc Omadine, alkalizing agents such as, for example, ammonia, monoethanolamine, 2-amino-2-methylpropanol and 2-amino-2-methylpropane-1,3-diol, other substances for adjusting the pH value, active substances, such as panthenol, pantothenic acid, allantoin, pyrrolidone carboxylic acids and salts thereof, plant extracts and vitamins, cholesterol, UV filters, consistency promoters, such as sugar esters, polyol esters or polyol alkyl ethers, fats and waxes, such as spermaceti, beeswax, montan wax, paraffins, fatty alcohols and fatty acid esters, fatty acid alkanolamides, complexing agents, such as EDTA, NTA and phosphonic acids, swelling and penetration agents, such as glycerol, propylene glycol monoethyl ether, carbonates, hydrogen carbonates, guanidines, ureas and primary, secondary and tertiary phosphates, opacifiers, such as latex, pearlescers, such as ethylene glycol mono- and distearate, propellents, such as propane/butane mixtures, $N_2O$, dimethyl ether, $CO_2$ and air and antioxidants.

To produce the colorants according to the invention, the constituents of the water-containing carrier are used in the usual quantities for this purpose. For example, emulsifiers are used in concentrations of 0.5 to 30% by weight while thickeners are used in concentrations of 0.1 to 25% by weight, based on the colorant as a whole.

Basically, the color is oxidatively developed with atmospheric oxygen or with an oxidizing agent present in or added to the colorant immediately before application.

In a first preferred embodiment, a chemical oxidizing agent is used. This is particularly advantageous in cases where human hair is to be not only colored, but also lightened. Particularly suitable oxidizing agents are hydrogen peroxide or addition products thereof with urea, melamine or alkali metal borate. In a particularly preferred variant of this embodiment, the colorant according to the invention is mixed immediately before application with the preparation of an oxidizing agent, more particularly an aqueous $H_2O_2$ solution. The ready-to-use hair coloring preparation formed should preferably have a pH value of 6 to 10. In a particularly preferred embodiment, the hair colorant is used in a mildly alkaline medium. The application temperatures may be in the range from 15 to 40° C. After a contact time of about 30 minutes, the hair colorant is removed from the hair to be colored by rinsing. There is no need for the hair to be washed with a shampoo where a carrier of high surfactant content, for example a coloring shampoo, has been used.

In the particular case of hair which is difficult to color, the preparation containing the oxidation dye precursors may be applied to the hair without preliminary mixing with the oxidation component. The oxidation component is applied after a contact time of 20 to 30 minutes, optionally after rinsing. After another contact time of 10 to 20 minutes, the hair is rinsed and, if desired, shampooed.

In a second embodiment, the color is developed with atmospheric oxygen. In this case, it is of advantage to add an oxidation catalyst to the colorant according to the invention.

Suitable oxidation catalysts are metal salts and metal complexes, transition metals being preferable. Copper, manganese, cobalt, selenium, molybdenum, bismuth and ruthenium compounds are preferred. Copper(II) chloride, sulfate and acetate can be preferred oxidation catalysts. Preferred metal complexes include the complexes with ammonia, ethylenediamine, phenanthroline, triphenyl phosphine, 1,2-diphenyl phosphinoethane, 1,3-diphenyl phosphinopropane or amino acids. The same colorant may of course also contain several oxidation catalysts. Particulars of the production of suitable catalysts can be found in the corresponding disclosure of EP 0 709 365 A1 (page 4, lines 19 to 42) to which reference is expressly made.

The oxidation may also be carried out with enzymes. In this case, the enzymes may be used both to produce oxidizing per compounds and to enhance the effect of an oxidizing agent present in small quantities. One example of an enzymatic process is the procedure where the effect of small quantities (for example 1% and less, based on the colorant as a whole) of hydrogen peroxide is enhanced by peroxidases.

The present invention also relates to the use of diaminoalkanes corresponding to general formula (I) in claim 1 for coloring keratin fibers.

The compounds corresponding to general formulae (VII), (VIIa), (VII)' and (IX)' are intermediate products for the production of the compounds corresponding to general formula (I). Their structures and production processes are described in detail in the Examples. It has also been found that these compounds are suitable as substantive dyes either on their own or in combination with other substantive dyes for coloring keratin fibers, more particularly hair. These compounds may also be used together with hair dye precursors of the secondary and primary intermediate type and, optionally, other substantive dyes in colorants for keratin fibers, more particularly hair, where the color is developed by oxidizing agents or air and catalysts.

The following Examples are intended to illustrate the invention.

EXAMPLES

1. General Production Processes 1.1. N, N'-bis-(2,4-diaminophenyl)-1,n-diaminoalkanes The compounds according to the invention corresponding to formula (I), which are derivatives of N,N'-bis-(2,4-diaminophenyl)-1,n-diaminoalkanes, may be prepared by several methods known in principle to the expert. The basic principles of these methods, which may be modified for the special compounds in accordance with general expert knowledge, are described in the following.

In a first process, the N,N'-bis-(2,4-diaminophenyl)-1,n-diaminoalkanes according to the invention corresponding to general formula (I) are prepared by reacting 2,4-dinitrohalobenzenes corresponding to general formula (II), where X=fluorine, chlorine, bromine or iodine, with 1,n-diaminoalkanes corresponding to formula (III) in which $R^9$ and $R^{10}$ may have the meanings defined in claim 1, in an alkaline reaction medium, optionally in the presence of phase transfer catalysts, to form N,N'-bis-(2,4-dinitrophenyl)-1,n-diaminoalkanes corresponding to general formula (IV):

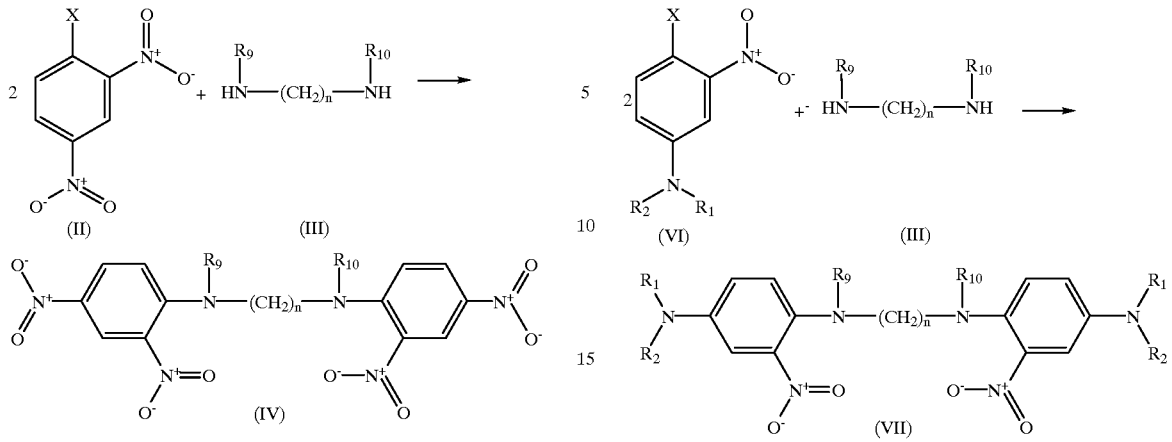

Suitable phase transfer catalysts are, for example, methyl or benzyl tri($C_{6-8}$) alkyl ammonium chloride. This reaction may optionally be carried out under pressure in an autoclave to obtain a complete reaction. The compounds corresponding to general formula (IV) are reduced to the compounds corresponding to general formula (V), optionally alkylated or alkoxylated to the compounds of general formula (I) according to the invention and optionally converted into their salts with inorganic or organic acids.

Basically, the reduction may be carried out in steps, i.e. the two nitro groups in the ortho position are first selectively reduced and then alkylated or alkoxylated or the two nitro groups in the para-position are subjected first to selective reduction and then to alkylation or hydroxyalkylation. Reduction of the remaining nitro functions and optionally subsequent alkylation or hydroxyalkylation then gives the compounds according to the invention corresponding to general formula (I).

After reduction and optionally further alkylation or alkoxylation, the compounds according to the invention corresponding to general formula (I) are obtained and are optionally converted with an inorganic or organic acid into a salt.

In a third process, the N,N'-bis-(2,4-diaminophenyl)-1,n-diaminoalkanes according to the invention corresponding to general formula (I) may be obtained by initially reacting substituted 2-amino-4-nitrohalobenzenes corresponding to general formula (VIa), in which $R_1$ and $R_2$ are as defined in claim 1, with 1,n-diaminoalkanes corresponding to general formula (III) to form compounds corresponding to general formula (VIIa).

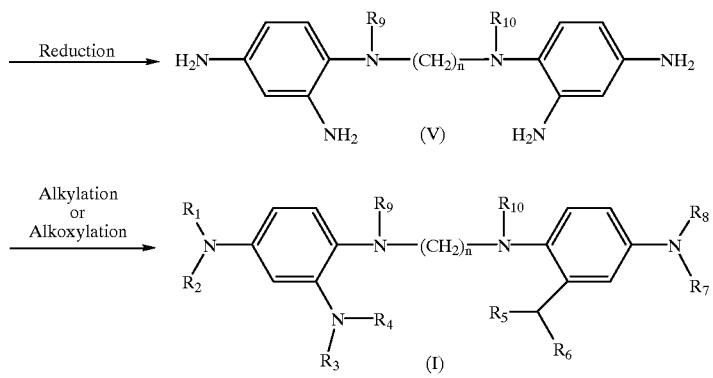

In a second process, the N,N'-bis-(2,4-diaminophenyl)-1,n-diaminoalkanes according to the invention corresponding to general formula (I) may be obtained by initially reacting substituted 4-amino-2-nitrohalobenzenes corresponding to general formula (VI), in which $R_5$ and $R_6$ are as defined in claim 1, with 1,n-diaminoalkanes corresponding to general formula (III), in which $R^9$ and $R^{10}$ are as already defined, optionally in the presence of phase transfer catalysts, to form compounds corresponding to general formula (VII):

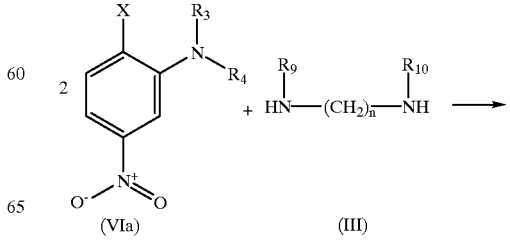

-continued

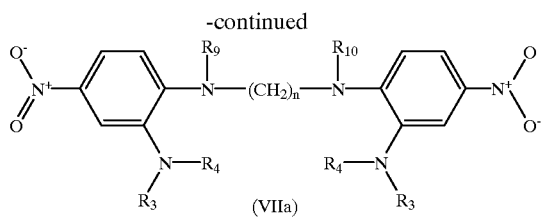

After reduction and optionally further alkylation or alkoxylation, the compounds according to the invention corresponding to general formula (I) are obtained and are optionally converted with an inorganic or organic acid into a salt.

The first stage of these processes essentially comprises exchanging a halogen substituent for an amine substituent at the phenyl ring. The known processes are normally carried out with an excess of amine of about 40 to 80%. The products are obtained in yields of about 90% and with a purity of 95 to 96%. It has now surprisingly been found that higher yields can be obtained for the same or better purities and a faster conversion if the amine excess is 30% or less, more particularly 5 to 10 mole-%, based on the quantities of compound (II), (VI) or (VIa) used. The reaction of the amines corresponding to general formula (III) with the compounds (II), (VI) or (VIa) is preferably carried out in the presence of alkali metal carbonates as acid-binding agents. In another preferred embodiment, the reaction is carried out in an organic solvent. Moreover, the reaction is preferably carried out under a pressure of 1 to 15 bar, more preferably under a pressure of 1 to 8 bar and most preferably under a pressure of 1 to 2.5 bar.

The compounds corresponding to general formula (VII) or (VIIa) can be obtained by alkylation or alkoxylation of compounds corresponding to formula (VII) or (VIIa), where $R_1$ and $R_2$ or $R_3$ and R48=hydrogen. This can be done by reacting these compounds with dialkyl sulfate, alkyl halide or alkylene oxides in an inert solvent or by rearranging carbamates obtained therefrom by known methods and subsequently treating them with the alkylating agents mentioned above.

The reaction of the compound corresponding to general formula (V), (VII) or (VIIa) [$R_1$ and $R_2$, $R_3$ and $R_4$, $R_5$ and $R_6$ and/or $R_7$ and $R_8$=hydrogen] may be carried out by known methods with chloroformic acid-2-chloroethyl ester or chloroformic acid-3-chloropropyl ester and subsequent treatment of the chloroalkyl carbamates with a base.

The compounds corresponding to general formula (I) may be produced by reducing the compounds corresponding to general formula (IV), (VII) or (VIIa) with base metals or by catalytic reduction, optionally after alkylation or alkoxylation.

The catalytic reduction is carried out with standard catalysts, for example Raney nickel, palladium on active carbon or platinum on active carbon. The reaction temperature is between room temperature and 120° C. and preferably between 35 and 100° C. while the pressure is between normal pressure and 20 bar and preferably between 2 and 7 bar. The solvents used are standard solvents, such as water, toluene, glacial acetic acid, lower alcohols or ethers. After the reduction and removal of the catalyst, the product corresponding to general formula (I) may be isolated in free form by distilling off the solvent in an inert gas atmosphere, optionally after alkylation alkoxylation. Suitable alkylating agents are the known compounds dimethyl and diethyl sulfate while suitable alkoxylating agents are the known compounds ethylene oxide and propylene oxide. The product corresponding to general formula (I) is converted into a salt, preferably in an inert gas atmosphere, by adding a 1.0- to 1.1-equivalent quantity of an acid. The salt either precipitates directly or is obtained after removal of the solvent.

Suitable inorganic acids for salt formation are, for example, hydrochloric acid, sulfuric acid, phosphoric acid while suitable organic acids for salt formation are acetic acid, propionic acid, lactic acid or citric acid.

1.2. N,N'-bis-(2,5-diaminophenyl)-1,n-diaminoalkanes

Like the derivatives of N,N'-bis-(2,4-diaminophenyl)-1, n-diaminoalkanes, the compounds according to the invention corresponding to formula (I) which are derivatives of N,N'-bis-(2,5-diaminophenyl)-1,n-diaminoalkanes may also be prepared by these methods known in principle to the expert. The basic principles of these methods also, which may be modified for the special compounds in accordance with general expert knowledge, are described in the following.

In a first process, the N,N'-bis-(2,5-diaminophenyl)-1,n-diaminoalkanes according to the invention corresponding to general formula (I) are prepared by reacting 2,5-dinitrohalobenzenes corresponding to general formula (II)', where X=fluorine, chlorine, bromine or iodine, with 1,n-diaminoalkanes corresponding to general formula (III) in an alkaline reaction medium, optionally in the presence of phase transfer catalysts, to form N,N'-bis-(2,5-dinitrophenyl)-1,n-diaminoalkanes corresponding to general formula (IV)':

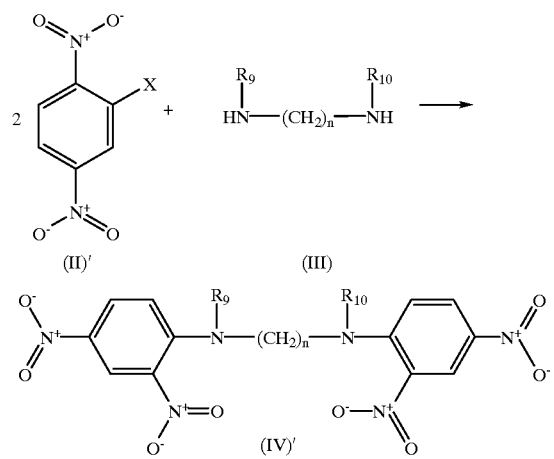

Suitable phase transfer catalysts are, for example, methyl or benzyl tri($C_{6-8}$) alkyl ammonium chloride. This reaction may optionally be carried out under pressure in an autoclave to obtain a complete reaction. The compounds corresponding to general formula (IV)' are reduced to the compounds corresponding to general formula (V)', optionally alkylated or alkoxylated to the compounds of general formula (I) according to the invention and optionally converted into their salts with inorganic or organic acids.

Basically, the reduction may be carried out in steps, i.e. the two nitro groups in the ortho position are first selectively reduced and then alkylated or alkoxylated or the two nitro groups in the meta-position are subjected first to selective reduction and then to alkylation or hydroxyalkylation. Reduction of the remaining nitro functions and optionally subsequent alkylation or hydroxyalkylation then gives the compounds according to the invention corresponding to general formula (I).

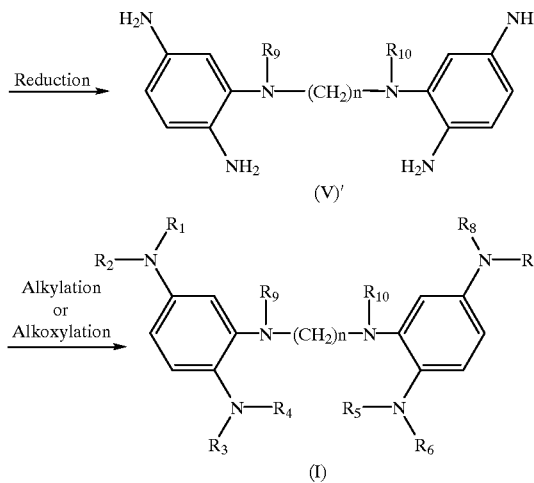

(V)'

(I)

In a second process, the N,N'-bis-(2,5-diaminophenyl)-1,n-diaminoalkanes according to the invention corresponding to general formula (I) may be obtained by initially reacting substituted 2-nitro-5-aminohalobenzenes corresponding to general formula (VI)', in which $R_1$ and $R_2$ are as defined above, with 1,n-diaminoalkanes corresponding to general formula (III) to form compounds corresponding to general formula (VII)':

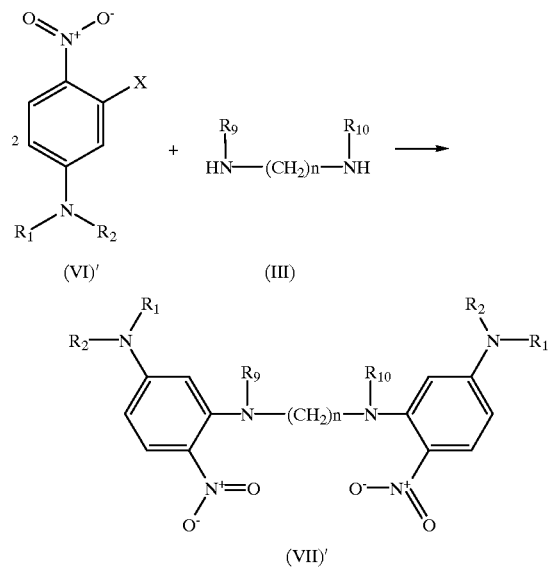

(VI)'   (III)

(VII)'

After reduction and optionally further alkylation or alkoxylation, the compounds according to the invention corresponding to general formula (I) are obtained and are optionally converted with an inorganic or organic acid into a salt.

In a third process, the N,N'-bis-(2,5-diaminophenyl)-1,n-diaminoalkanes according to the invention corresponding to general formula (I) may be obtained by initially reacting substituted 2-nitro-5-aminohalobenzenes corresponding to general formula (VIa)', in which $R_1$ and $R_2$ are as defined in claim 1, with 1,n-diaminoalkanes corresponding to general formula (III) to form compounds corresponding to general formula (VIII)'.

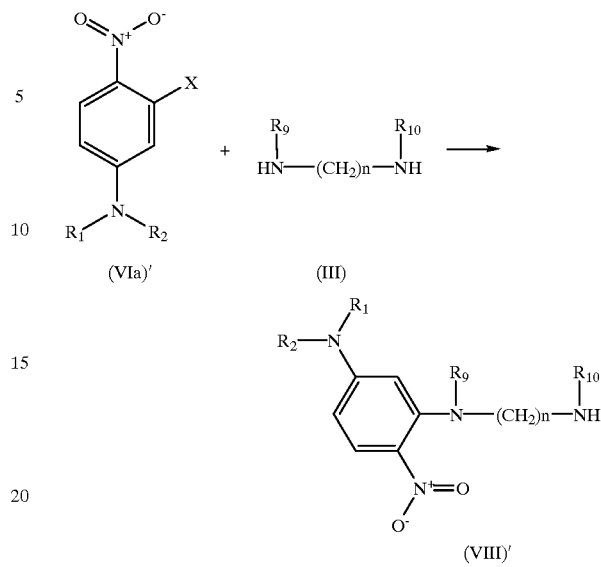

(VIa)'   (III)

(VIII)'

The intermediate product corresponding to general formula (VII)' may then be reacted with a compound corresponding to general formula (VIb), which bears other substituents $R_3$ and $R_4$ with the meaning defined above at its nitrogen atom, to form the mixed-substituted compounds corresponding to general formula (IX).

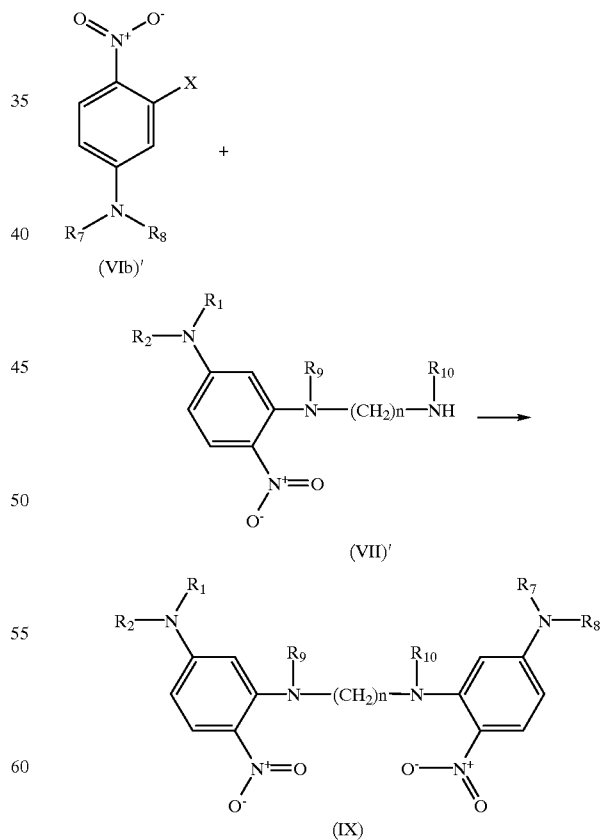

(VIb)'

(VII)'

(IX)

After reduction and optionally further alkylation or alkoxylation, the compounds (IX) give compounds corresponding to general formula (I) according to the invention.

The first stage of these processes essentially comprises exchanging a halogen substituent for an amine substituent at the phenyl ring. The known processes are normally carried out with an excess of amine of about 40 to 80%. The products are obtained in yields of about 90% and with a purity of 95 to 96%. It has now surprisingly been found that higher yields can be obtained for the same or better purities and a faster conversion if the amine excess is 30% or less, more particularly 5 to 10 mole-%, based on the quantities of compound (II)', (VI)', (VIa) or (VIb)' used. The reaction of the amines corresponding to general formula (III) with the compounds (II)', (VI)', (VIa)' or (VIb)' is preferably carried out in the presence of alkali metal carbonates as acid-binding agents. In another preferred embodiment, the reaction is carried out in an organic solvent. Moreover, the reaction is preferably carried out under a pressure of 1 to 15 bar, more preferably under a pressure of 1 to 8 bar and most preferably under a pressure of 1 to 2.5 bar.

The compounds corresponding to general formula (VII)' or (IX) can be obtained by alkylation or alkoxylation of compounds corresponding to general formula (VII)' or (IX), where $R_1$ and $R_2$ or $R_3$ and $R_4$=hydrogen. This can be done by reacting these compounds with dialkyl sulfate, alkyl halide or alkylene oxides in an inert solvent or by rearranging carbamates obtained therefrom by known methods and subsequently treating them with the alkylating agents mentioned above.

The reaction of the compound corresponding to general formula (VII)' or (IX) [$R_1$ and $R_2$ and $R_3$ and $R_4$=hydrogen] may be carried out by known methods with chloroformic acid-2-chloroethyl ester or chloroformic acid-3-chloropropyl ester and subsequent treatment of the chloroalkyl carbamates with a base.

The compounds corresponding to general formula (I) may be produced by reducing the compounds corresponding to general formula (IV)', (VII)' or (IX) with base metals or by catalytic reduction, optionally after alkylation or alkoxylation.

The catalytic reduction is carried out with standard catalysts, for example Raney nickel, palladium on active carbon or platinum on active carbon. The reaction temperature is between room temperature and 120° C. and preferably between 35 and 100° C. while the pressure is between normal pressure and 20 bar and preferably between 2 and 7 bar. The solvents used are standard solvents, such as water, toluene, glacial acetic acid, lower alcohols or ethers. After the reduction and removal of the catalyst, the product corresponding to general formula (I) may be isolated in free form by distilling off the solvent in an inert gas atmosphere, optionally after alkylation or alkoxylation. Suitable alkylating agents are the known compounds dimethyl and diethyl sulfate while suitable alkoxylating agents are the known compounds ethylene oxide and propylene oxide. The product corresponding to general formula (I) is converted into a salt, preferably in an inert gas atmosphere, by adding a 1.0- to 1.1-equivalent quantity of an acid. The salt either precipitates directly or is obtained after removal of the solvent.

1.3. Preparation of Special Compounds Corresponding to Formula (I)

The compounds prepared were characterized by IR spectra or IR(KBr pellet) and/or $^1$H-NMR spectra (in $D_6$-DMSO). Where the spectra are shown in the following, only the very strong and strong bands are mentioned in the case of the IR spectra. In the data on the $^1$H-NMR spectra, s=singlet, d=doublet, dd=doublet of the doublet, t=triplet, q=quartet, qi–quintet, m=multiplet, $^3$J and $^4$J=the couplings via three or four bonds and $H^3$, $H^4$, $H^5$ and $H^6$=the hydrogen atoms in positions 3, 4, 5 and 6 of the benzene rings.

1.3.1. Preparation of N,N'-bis-(2,4-diaminophenyl)-1,2-diaminoethane sulfate

Step a) N,N'-bis-(2,4-dinitrophenyl)-1,2-diaminoethane 20.4 g (0.1 mole) of 2,4-dinitrochlorobenzene and 3 g (0.05 mole) of 1,2-diaminoethane were introduced into 100 ml of 1,2-dimethoxyethane. 10.6 g (0.1 mole) of sodium carbonate were then added with stirring, the temperature rising to about 40° C. The mixture was then heated to 50° C. and left at that temperature for 2 hours until the reaction was complete. The yellow product precipitated was filtered off under suction, washed twice with about 100 ml of water and dried in vacuo at 40° C.

Yield: 19.9 g (100% of the theoretical); IR: 3114 cm$^{-1}$ (v $CH_{Ar}$), 2926, 2873 cm$^{-1}$ (v CH), 1602 cm$^{-1}$ (v C═C), 1531, 1510 cm$^{-1}$ ($v_{as}$ $NO_2$), 1327 cm$^{-1}$ ($v_s$ $NO_2$).

$^1$H-NMR: 8.67 ppm (2 $H^3$, d, $^4J_{H,H}$=2.68 Hz); 8.34 ppm (2 $H^5$, dd, $^3J_{H,H}$=9.48 Hz $^4J_{H,H}$=2.75 Hz); 7.40 ppm (2 $H^6$, d, $^3J_{H,H}$=9.50 Hz); 3.64 ppm (8 H. s, $NCH_2$).

Step b) N,N'-bis-(2,4-diaminophenyl)-1,2-diaminoethane sulfate 150 ml of methanol were introduced into a 0.3 liter autoclave, 17 g (0.04 mole) of N,N'-bis-(2,4-nitrophenyl)-1,2-diaminoethane were dissolved therein and 1 g of palladium on active carbon 10% (Degussa) was added. After the autoclave had been closed and blanketed with nitrogen, hydrogenation was carried out under a pressure of 3 bar and at a temperature of 35 to 40° C. until no more hydrogen was taken up. The mixture was emptied onto a pressure filter, the residue was dissolved in 100 ml of N-methyl pyrrolidone at 100° C., the catalyst was filtered off using a pressure filter and, after cooing of the filtrate to 5–10° C., 9.8 g (0.1 mole) of 80% sulfuric acid were added dropwise. The jelly-like precipitate was stirred with 200 ml of methanol. The crystallized product was filtered off under suction, washed with methanol and dried.

Yield: 17.3 g (46.7% of the theoretical); Melting point: >200° C.

1.3.2. Preparation of N,N'-bis-(2,4diaminophenyl)-1,3diaminopropane sulfate

Step a) N,N'-bis-(2,4-dinitrophenyl)-1,3-diaminopropane

The compound is prepared in the same way as in Example 1.3.1. step a) by reacting 2,4-dinitrochlorobenzene with 1,3-diaminopropane.

Yield: 19.6 g (48.3% of the theoretical)

Step b) N,N'-bis-(2,4-diaminophenyl)-1,3-diaminopropane sulfate

Step b) is carried out in the same way as Eample 1.3.1. step b) by catalytic reduction of the compound obtained in step a).

Yield: 20.6 g (53.6% of the theoretical)

1.3.3. Preparation of N,N'-bis-(2,5-diaminophenyl)-1,2-diaminoethane sulfate

Step a) N,N'-bis-(2,5-dinitrophenyl)-1,2-diaminoethane 20.3 g (0.1 mole) of 2,5-dinitrochlorobenzene and 3.0 g (0.05 mole) of diaminoethane were introduced into 55 ml of 1,2-dimethoxyethane. 4 g (0.1 mole) of sodium hydroxide (prills) were then added with stirring, the temperature rising to about 40° C. The mixture was then heated under reflux for 2 hours until the reaction was complete. 100 ml of water were added and the product was precipitated by stirring. The precipitated product was filtered under suction, washed twice with about 100 ml of water and dried in vacuo at 40° C.

Yield: 19.6 g (93.7% of the theoretical); IR: 3114 cm$^{-1}$ (v $CH_{Ar}$), 2926, 2873 cm$^{-1}$ (v CH), 1602 cm$^{-1}$ (v C═C), 1531, 1510 cm$^{-1}$ ($v_{as}$ $NO_2$), 1327 cm$^{-1}$ ($v_s$ $NO_2$). $^1$H-NMR: 8.67 ppm (2 $H^3$, d, $^4J_{H,H}$=2.68 Hz); 8.34 ppm (2 $H^4$, dd, $^3J_{H,H}$=

9.48 HZ, $^4J_{H,H}$=2.75 Hz); 7.40 ppm (2 H$^6$, d, $^3J_{H,H}$=9.50 Hz); 3.64 ppm (8 H, s, NCH$_2$).

Step b) N,N'-bis-(2,5-diaminophenyl)-1,2-diaminoethane sulfate 150 ml of methanol were introduced into a 0.3 liter autoclave, 16.7 g (0.2 mole) of N,N'-bis-(2,5-dinitrophenyl)-1,2-diaminoethane were dissolved therein and 2 g of palladium on active carbon 10% (Degussa) were added. After the autoclave had been closed and blanketed with nitrogen, hydrogenation was carried out under a pressure of 3 bar and at a temperature of 35 to 40° C. until no more hydrogen was taken up. The mixture was emptied onto a pressure filter, the residue was dissolved in 100 ml of N-methyl pyrrolidone at 100° C., the catalyst was filtered off using a pressure filter and, after cooing of the filtrate to 5–10° C., 9.8 g (0.1 mole) of 80% sulfuric acid were added dropwise. The jelly-like precipitate was stirred with 200 ml of methanol. The crystallized product was filtered off under suction, washed with methanol and dried.

Yield: 16.8 g (84.9% of the theoretical); Melting point: >200° C.

1.3.4. Preparation of N,N'-bis-(2-amino-5-dimethylaminophenyl)-1,2-diaminoethane sulfate Step a) N,N'-bis-(2-nitro-5-dimethylaminophenyl)-1,2-diaminoethane 100 ml of 1,2-dimethoxyethane, 20.1 g (0.1 mole) of 2-nitro-5-N,N-dimethylaminochlorobenzene, 6.0 g (0.1 mole) of 1,2-diaminoethane, 5.3 g (0.05 mole) of potassium carbonate and 0.25 g of methyl tri(C$_{6-8}$)alkyl ammonium chloride (70% in isopropanol) were introduced into a 0.3 l autoclave. The mixture was heated for 8 hours at 125° C. After cooling to 40° C., the undissolved salts were filtered off and 100 ml of water were added to the mother liquor. The product precipitated was filtered off under suction and dried.

Yield: 41.0 g (99% of the theoretical);

Step b) N,N'-bis-(2-amino-5-dimethylaminophenyl)-1,2-diaminoethane sulfate

Step b) is carried out in the same way as Example 1.3.3. step b) by catalytic reduction of the product obtained in step a).

Yield: 20.5 g (45.3% of the theoretical)

2. Coloring
2.1. Colorants:
Creme-based C1

| | |
|---|---|
| Sodium lauryl sulfate (70%) | 2.5 g |
| Oleic acid | 1.0 g |
| Sodium sulfite, anhydrous | 0.6 g |
| Cetostearyl alcohol | 12.0 g |
| Myristyl alcohol | 6.0 g |
| Propylene glycol | 1.0 g |
| Ammonia, 25% | 10.0 g |
| Oxidation dye precursors | x.x g |
| Water | to 100 g |

Gel-based G1

| | |
|---|---|
| Oleic acid | 12.0 g |
| Isopropanol | 12.0 g |
| Nonoxynol A | 5.0 g |
| Ammonia, 25% | 10.0 g |
| Sodium sulfite, anhydrous | 0.5 g |
| Oxidation dye precursors | x.x g |
| Water | to 100 g |

2.2. Oxidation dye precursors
Corresponding to Formula (I)
(I-1) N,N'-bis-(2,4-diaminophenyl)-1,3-diaminopropane sulfate
(I-2) N,N'-bis-(2,5-diaminophenyl)-1,2-diaminoethane sulfate Primary Intermediates
(P-1) p-aminophenol
(P-2) 2-(2'-hydroxyethyl)-p-phenylenediamine sulfate
(P-3) p-phenylenediamine dihydrochloride
(P-4) 2,5-diaminotoluene sulfate
(P-5) 4-amino-m-cresol Secondary Intermediates
(S-1) resorcinol
(S-2) m-aminophenol
(S-3) 4-amino-2-hydroxytoluene
(S-4) 2-amino-4-hydroxyethylaminoanisole 2.3. Procedure 50 g of the colorant were mixed just before use with 50 g of H$_2$O$_2$ solution (6% in water) and the resulting mixture was applied by brush to 100% grey hair (4 g of colorant per g of hair). After a contact time of 30 minutes at room temperature, the creme-based colorant was rinsed off and the hair was dried. In the case of the gel base, the hair was shampooed and dried after the colorant had been rinsed off.

2.4. Results

The coloring results are set out in the following Table:

| Base | Oxidation dye precursors | Color |
|---|---|---|
| C1 | 1.92 g I-1 + 1.09 g P-1 | Uniform red-brown |
| C1 | 1.92 g I-1 + 1.52 g P-2 | Uniform brown |
| C1 | 1.92 g I-1 + 1.08 g P-3 | Uniform black |
| C1 | 1.92 g I-1 + 1.22 g P-4 | Uniform brown with violet reflection |
| G1 | 1.92 g I-1 + 1.23 g P-5 | Light red blond with reddish reflection |
| C1 | 1.92 g I-1 + 1.10 g S-1 | Uniform red-brown |
| C1 | 1.92 g I-1 + 1.09 g S-2 | Uniform brown |
| C1 | 1.92 g I-1 + 1.05 g S-3 | Uniform dark blue |
| C1 | 1.92 g I-1 + 2.80 g S-4 | Uniform black |
| C1 | 2.47 g I-2 + 1.10 g S-1 | Uniform red-brown with green reflection |
| C1 | 2.47 g I-2 + 1.09 g S-2 | Uniform blue with green reflection |
| C1 | 2.47 g I-2 + 1.23 g S-3 | Uniform azure blue |
| C1 | 2.47 g I-2 + 2.50 g S-4 | Uniform marine blue |
| C1 | 2.47 g I-2 + 1.09 g P-1 | Uniform red brown |
| C1 | 2.47 g I-2 + 1.52 g P-2 | Uniform silver grey |
| C1 | 2.47 g I-2 + 1.08 g P-3 | Uniform blue-black |
| C1 | 2.47 g I-2 + 1.22 g P-4 | Uniform brown |
| G1 | 2.47 g I-2 + 1.23 g P-5 | Light golden blond with reddish reflection |

We claim:

1. Diaminoalkane of the general formula (I) or a physiologically compatible salt thereof with an inorganic or organic acid:

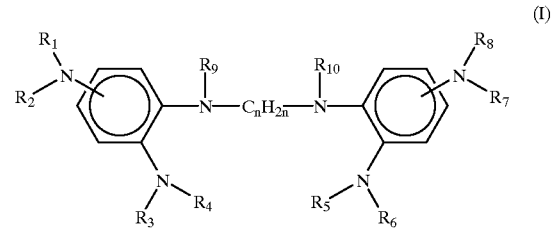

(I)

wherein R$_1$ to R$_{10}$ independently of one another are hydrogen, (C$_{1-4}$)-alkyl, hydroxy-(C$_{2-3}$)-alkyl, (C$_{1-4}$)-alkoxy-(C$_{2-3}$)-alkyl, amino-(C$_{2-3}$)-alkyl, or 2,3-dihydroxypropyl, n is an integer of 1 to 6, and the groups —NR$_1$R$_2$ and —NR$_7$R$_8$ are either in positions 4 and 4' or in positions 5 and 5'.

2. A diaminoalkane according to claim 1, wherein the groups —NR$_1$R$_2$ and —NR$_7$R$_8$ are identical and the groups —NR$_3$R$_4$ and —NR$_5$R$_6$ are identical.

3. An oxidation colorant comprising a diaminoalkane of the general formula (I) or a physiologically compatible salt thereof with an inorganic or organic acid:

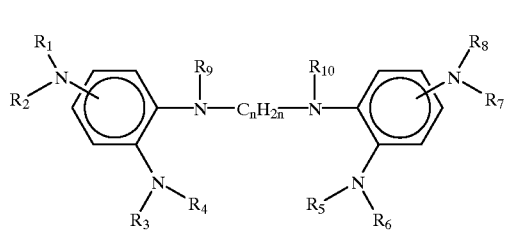
(I)

wherein $R_1$ to $R_{10}$ independently of one another are hydrogen, $(C_{1-4})$-alkyl, hydroxy-$(C_{2-3})$-alkyl, $(C_{1-4})$-alkoxy-$(C_{2-3})$-alkyl, amino-$(C_{2-3})$-alkyl or 2,3-dihydroxypropyl, n is an integer of 1 to 6, and the groups —$NR_1R_2$ and —$NR_7R_8$ are either in positions 4 and 4' or in positions 5 and 5' as an oxidation dye precursor.

4. An oxidation colorant according to claim 3, comprising 0.001% to 10% by weight of the diaminoalkane or physiologically compatible salt thereof.

5. An oxidation colorant according to claim 3, comprising 0.1% to 5% by weight of the diaminoalkane or physiologically compatible salt thereof.

6. An oxidation colorant according to claim 3, further comprising an additional oxidation dye precursor which is a secondary intermediate.

7. An oxidation colorant according to claim 5, further comprising an additional oxidation dye precursor which is a secondary intermediate.

8. An oxidation colorant according to claim 3, further comprising an additional oxidation dye precursor which is a primary intermediate.

9. An oxidation colorant according to claim 7, further comprising an additional oxidation dye precursor which is a primary intermediate.

10. An oxidation colorant according to claim 3, further comprising a substantive dye.

11. An oxidation colorant according to claim 9, further comprising a substantive dye.

12. An oxidation colorant according to claim 3, wherein the groups —$NR_1R_2$ and —$NR_7R_8$ are identical and —$NR_3R_4$ and —$NR_5R_6$ are identical.

13. An oxidation colorant according to claim 12, comprising 0.001% to 10% by weight of the diaminoalkane or physiologically compatible salt thereof.

14. An oxidation colorant according to claim 12, comprising 0.1% to 5% by weight of the diaminoalkane or physiologically compatible salt thereof.

15. An oxidation colorant according to claim 13, further comprising an additional oxidation dye precursor which is a secondary intermediate.

16. An oxidation colorant according to claim 15, further comprising an additional oxidation dye precursor which is a primary intermediate.

17. An oxidation colorant according to claim 16, further comprising a substantive dye.

18. An oxidation colorant according to claim 17, further comprising a salt or complex of a metal.

19. An oxidation colorant according to claim 18, wherein the metal is selected from the group consisting of copper, manganese, cobalt, selenium, molybdenum, bismuth, and ruthenium.

20. An oxidation colorant according to claim 3, wherein in formula (I) $R_1$ to $R_8$ are independently selected from the group consisting of hydrogen, methyl, ethyl, 2-hydroxyethyl, 2-aminoethyl, and 2,3-dihydroxypropyl, $R_9$ and $R_{10}$ are hydrogen, and n=2 or 3.

21. A method of coloring keratin fiber, comprising the step of contacting a keratin fiber with an effective amount of the colorant of claim 3 for coloring the fiber.

* * * * *